United States Patent
Nastacio

(10) Patent No.: US 9,251,545 B2
(45) Date of Patent: *Feb. 2, 2016

(54) RIGHTS MANAGEMENT FOR CONTENT AGGREGATORS

(71) Applicant: International Business Machines Corporation, Armonk, NY (US)

(72) Inventor: Denilson Nastacio, Apex, NC (US)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/837,341

(22) Filed: Mar. 15, 2013

(65) Prior Publication Data

US 2014/0283114 A1   Sep. 18, 2014

(51) Int. Cl.

| | |
|---|---|
| G06F 17/30 | (2006.01) |
| G06F 21/10 | (2013.01) |
| H04L 29/06 | (2006.01) |
| G06Q 50/18 | (2012.01) |
| G06Q 10/10 | (2012.01) |
| G06F 21/62 | (2013.01) |
| H04L 29/08 | (2006.01) |
| G06F 19/00 | (2011.01) |

(52) U.S. Cl.
CPC ............ *G06Q 50/182* (2013.01); *G06F 19/322* (2013.01); *G06F 21/10* (2013.01); *G06F 21/6254* (2013.01); *G06F 21/6263* (2013.01); *G06Q 10/10* (2013.01); *H04L 63/10* (2013.01); *H04L 67/02* (2013.01)

(58) Field of Classification Search
USPC ............................. 726/27; 713/153; 380/212
See application file for complete search history.

(56) References Cited

U.S. PATENT DOCUMENTS

| | | | |
|---|---|---|---|
| 7,999,728 B2 | 8/2011 | Chen et al. | |
| 8,103,590 B2 | 1/2012 | Quoc et al. | |
| 2004/0010707 A1* | 1/2004 | Johnson et al. | 713/200 |
| 2004/0167858 A1* | 8/2004 | Erickson | 705/55 |
| 2005/0278258 A1 | 12/2005 | O—Donnell et al. | |
| 2006/0173985 A1* | 8/2006 | Moore | 709/223 |
| 2006/0253910 A1* | 11/2006 | Yamamichi et al. | 726/31 |

(Continued)

FOREIGN PATENT DOCUMENTS

| | | |
|---|---|---|
| CN | 101281630 A | 10/2008 |
| GB | 2398712 A | 8/2004 |

OTHER PUBLICATIONS

Squicciarini, Anna, Smitha Sundareswaran, and Dan Lin. "Preventing information leakage from indexing in the cloud." Cloud Computing (CLOUD), 2010 IEEE 3rd International Conference on. IEEE, 2010.*

(Continued)

*Primary Examiner* — Michael Simitoski
(74) *Attorney, Agent, or Firm* — Alexa L. Ashworth; Ian A. McKee

(57) ABSTRACT

An arbitrator receives a request to use a plurality of content in an aggregation. The arbitrator determines whether there exist proper rights to use the plurality of content in the aggregation. The requestor is communicated whether permission is granted. The determination may include negotiating for extending right of use by an arbitrator. This negotiation may communicate with content hosting service(s) or the content author(s). The determining step retrieves, stores, and maintains rights information to and from an information store which is accessible by the rights management system.

11 Claims, 5 Drawing Sheets

(56) References Cited

U.S. PATENT DOCUMENTS

| | | |
|---|---|---|
| 2007/0078773 A1* | 4/2007 | Czerniak .......................... 705/57 |
| 2007/0083380 A1* | 4/2007 | Martinez ........................... 705/1 |
| 2007/0083762 A1* | 4/2007 | Martinez ....................... 713/176 |
| 2007/0106551 A1 | 5/2007 | McGucken |
| 2007/0198364 A1* | 8/2007 | Quoc et al. ....................... 705/26 |
| 2007/0204308 A1* | 8/2007 | Nicholas et al. ................ 725/86 |
| 2007/0219910 A1* | 9/2007 | Martinez .......................... 705/51 |
| 2008/0004120 A1* | 1/2008 | Van Luchene et al. .......... 463/42 |
| 2008/0082381 A1* | 4/2008 | Muller et al. ..................... 705/7 |
| 2008/0319771 A1* | 12/2008 | Shriver-Blake ................... 705/1 |
| 2009/0070371 A1* | 3/2009 | Cunningham et al. ..... 707/104.1 |
| 2009/0100013 A1* | 4/2009 | Fein et al. ......................... 707/3 |
| 2009/0209286 A1 | 8/2009 | Bentley et al. |
| 2011/0161091 A1 | 6/2011 | Freishtat et al. |
| 2011/0162089 A1* | 6/2011 | Hinton et al. ................... 726/30 |
| 2011/0179161 A1 | 7/2011 | Guy et al. |
| 2011/0296517 A1 | 12/2011 | Grigoriev et al. |
| 2012/0017266 A1* | 1/2012 | DiChiara et al. .................. 726/4 |
| 2012/0041829 A1* | 2/2012 | Rothschild et al. .......... 705/26.1 |
| 2013/0006865 A1* | 1/2013 | Spates ............................. 705/50 |
| 2013/0110978 A1* | 5/2013 | Gordon et al. ................ 709/218 |
| 2013/0174280 A1* | 7/2013 | Fujimori ......................... 726/30 |
| 2013/0179475 A1* | 7/2013 | Fujimori ....................... 707/802 |
| 2014/0279578 A1 | 9/2014 | Nastacio |

OTHER PUBLICATIONS

Wiederhold, Gio. "Mediation to deal with heterogeneous data sources." Interoperating Geographic Information Systems. Springer Berlin Heidelberg, 1999. 1-16.*

Abelson, Hal, et al. ccREL: The creative commons rights expression language. Technical report, Creative Commons, 2008. http://wiki.creativecommons.org/Image: Ccrel-1.0. pdf, 2008.*

Copyright Clearance Center. "Temple University Press Increases Rights Revenue and Reduces Costs with CCC's Rights Licensing Services", 2007.*

Stim, Richard. Getting permission: how to license & clear copyrighted materials online & off. Chapter 10. Nolo, 2013.*

Yu et al.; "TBDRM: A TPM-Based Secure DRM Architecture"; 2009 International Conference on Computational Science and Engineering; IEEE Computer Society; IEEE 2009; pp. 671-677.

"OAuth"; Wikipedia; Printed Dec. 19, 2012; <http://en.wikipedia.org/wiki/OAuth>.

* cited by examiner

RIGHTS MANAGEMENT FOR CONTENT AGGREGATORS

FIELD OF THE INVENTION

The present invention relates generally to the field of collaborative applications and more particularly to management of content applications over data communications networks.

BACKGROUND OF THE INVENTION

Online data aggregators are known. Such online data aggregators may offer aggregation services on a standalone basis or in conjunction with other services, such as portfolio tracking and on-line bill payment provided as a website service. Many established companies with an Internet presence appear to recognize the need of offering an aggregation service to enhance other web-based services which can attract more visitors. Offering a data aggregation service to a website is attractive because of the potential that it will frequently draw users of the service to the hosting website.

Over time, the transfer of large amounts of account data from the account provider to the aggregator's server could develop into a comprehensive profile of a user. The user's profile may include: (i) their banking; (ii) credit card transactions and balances; (iii) securities transactions and portfolios; and (iv) travel history and travel preferences. As the sensitivity to data protection considerations grows, it is likely there will be a considerable focus on the extent to which data aggregators may seek to use data either for their own purposes or to share it on some basis.

SUMMARY

Embodiments of the present invention provide for a program product, system, and method in which an arbitrator of a rights management system receives a request to use a plurality of content in an aggregation. The arbitrator determines whether there exist proper rights to use the plurality of content in the aggregation. The requestor is communicated whether permission is granted. The determination may include negotiating for extending right of use by an arbitrator. This negotiation may communicate with content hosting service(s) or the content author(s). The determining step retrieves, stores, and maintains rights information to and from an information store which is accessible by the rights management system.

DETAILED DESCRIPTION

Figure 1:
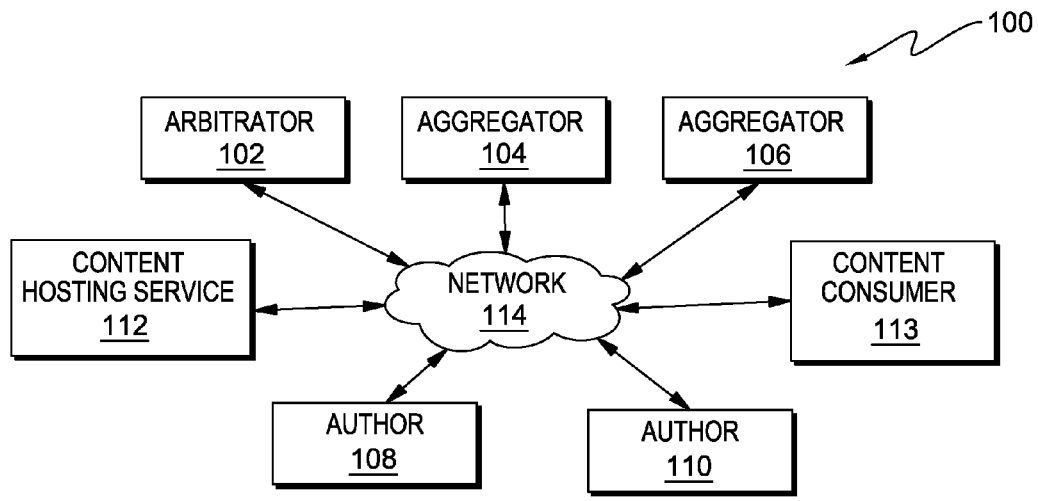
FIG. 1 is a schematic view of a distributed data processing system according to an embodiment of the present invention.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer-readable medium(s) having computer-readable program code/instructions embodied thereon.

Any combination of computer-readable media may be utilized. Computer-readable media may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Program code embodied on a computer-readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java (note: the term(s) "Java" may be subject to trademark rights in various jurisdictions throughout the world and are used here only in reference to the products or services properly denominated by the marks to the extent that such trademark rights may exist), Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

The present invention will now be described in detail with reference to the Figures. FIGS. 1, 2A, 2B, and 2C collectively make up a functional block diagram illustrating various portions of distributed data processing system 100, including: network 114, arbitrator 102, aggregators 104 and 106, authors 108 and 110, content hosting service 112, and content consumer 113; arbitration service computer 200; aggregator computer 250; content author computer 290; communication units 202, 252, 253; processors 204, 254, 255; input/output (i/o) units 206, 256, 257; memory devices 208, 258, 259; persistent storage devices 210, 260, 261; display devices 212, 262, 263; external device sets 214, 264, 265; random access memory (RAM) devices 230, 270, 271; cache memory devices 232, 272, 273; modules (mods) arbitration service s/w (software) 240, collection s/w 280, aggregation s/w 282, arbitration interface s/w 284 (3 locations), and content author s/w 286. In particular, arbitrator 102 includes an arbitration service computer 200 of computer sub-system 201, aggregators 104 and 106 each include an aggregator computer 250 of computer sub-system 251, and authors 108 and 110 each include a content author computer 290 of computer sub-system 254.

It should be appreciated that FIGS. 1, 2A, 2B, and 2C, taken together, provide only an illustration of one implementation (that is, system 100) and do not imply any limitations with regard to the environments in which different embodiments may be implemented. Many modifications to the depicted environment may be made, especially with respect to current and anticipated future advances in cloud computing, distributed computing, smaller computing devices, network communications and the like.

Figure 2A:
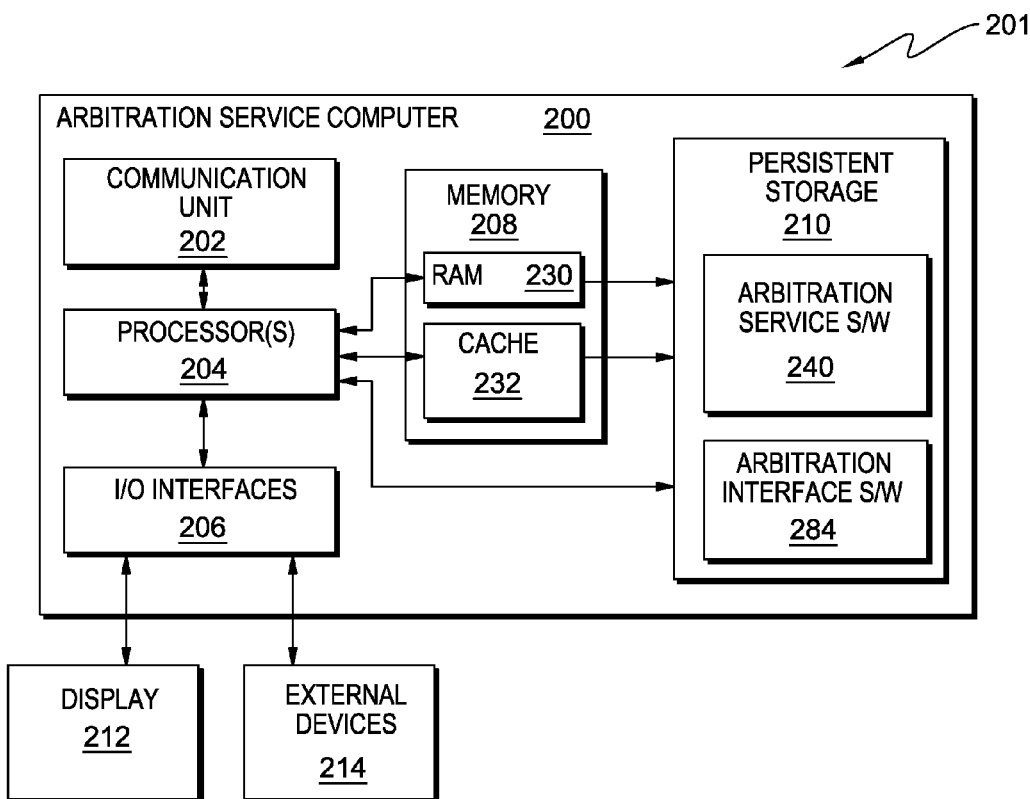
FIG. 2A is a schematic view of a portion of the distributed data processing system of FIG. 1.
Figure 2B:
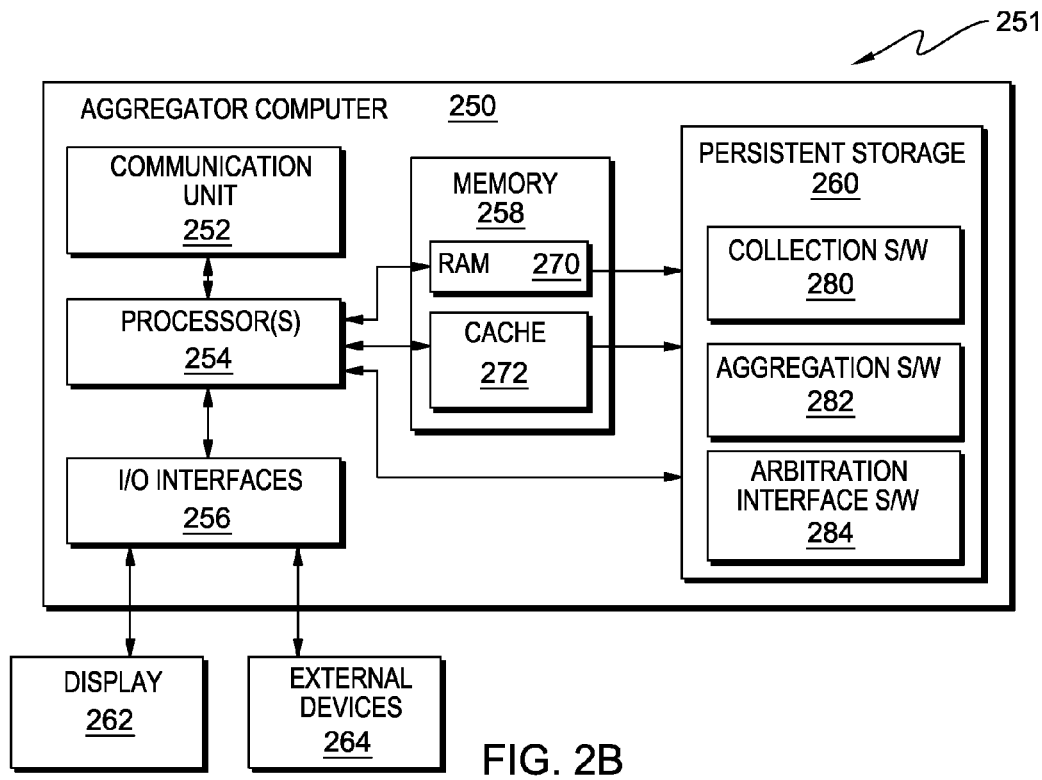
FIG. 2B is a schematic view of a portion of the distributed data processing system of FIG. 1.

As shown in FIG. 2A, computer sub-system 201 is, in many respects, representative of the various computer sub-system(s) in the present invention. Accordingly, several portions of computer sub-system 201 will now be discussed in the following paragraphs.

Computer sub-system 201 may be a laptop computer, tablet computer, netbook computer, personal computer (PC), a desktop computer, a personal digital assistant (PDA), a smart phone, or any programmable electronic device capable of communicating in distributed data processing system 100 via network 114. Arbitration service s/w 240 is a representative software module, and is a collection of machine readable instructions and data that is used to create, manage and control certain software functions that will be discussed in detail below.

Computer sub-system 201 is capable of communicating with other computer sub-systems via network 114 (see FIG. 1), such as computer sub-systems 251 and 254, for example. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between systems.

As further shown in FIG. 2A, computer sub-system 201 is shown as a block diagram with many double arrows. These double arrows (no separate reference numerals) represent a communications fabric, which provides communications between various components of sub-system 201. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for sub-system 201; and/or (ii) devices external to sub-system 201 may be able to provide memory for sub-system 201.

Arbitration service s/w 240 is in many respects representative of the various software modules of the present invention and is stored in persistent storage 210 for access and/or execution by one or more of the respective computer processors 204, usually through one or more memories of memory 208. Persistent storage 210 is at least more persistent than a signal in transit is, but the persistent storage may, of course, be substantially less persistent than permanent storage. Arbitration service s/w 240 may include both machine readable and performable instructions and/or substantive data (e.g., the type of data stored in a database, etc.). In this particular embodiment, persistent storage 210 includes a magnetic hard disk drive. To name some possible variations, persistent storage 210 may include a solid state drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 201 via network 114. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface(s) 206 allows for input and output of data with other devices that may be connected locally in data communication with arbitration service computer 200. For example, I/O interface 206 provides a connection to external devices 214. External devices 214 will typically include devices such as a keyboard, keypad, a touch screen, and/or some other suitable input device. External devices 214 can also include portable computer-readable storage media such as, for example, thumb drives, portable optical or magnetic disks, and memory cards. Software and data used to practice embodiments of the present invention, for example, arbitration service s/w 240, can be stored on such portable computer-readable storage media. In these embodiments the relevant software may (or may not) be loaded, in whole or in part, onto persistent storage device 210 via I/O interface 206. I/O interface 206 also connects in data communication with display 212.

Display 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Figure 3:
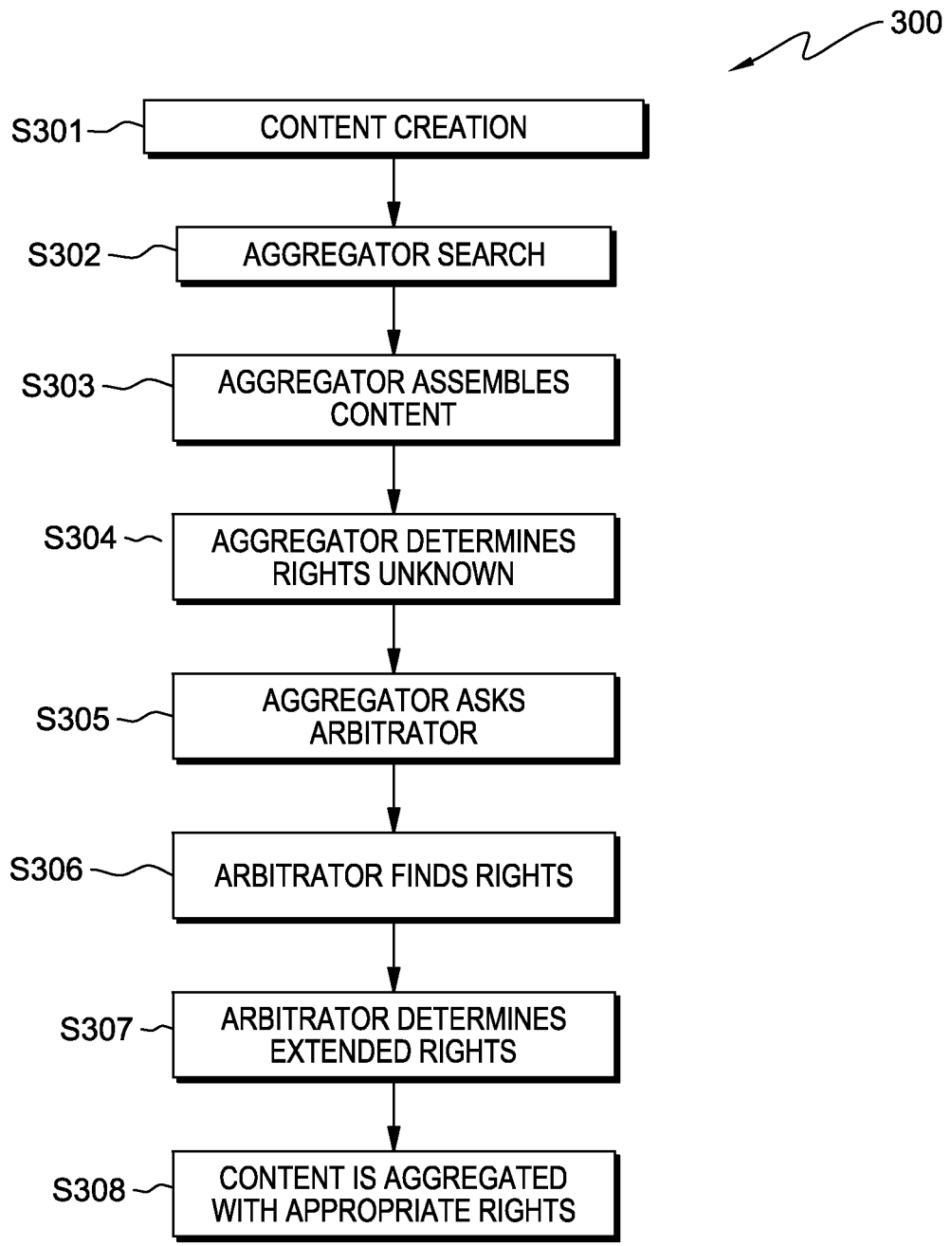
FIG. 3 depicts a flowchart illustrating steps followed within a distributed data processing system according to an embodiment of the present invention.

FIG. 3 depicts a flowchart illustrating process 300 in accordance with an embodiment of the present invention. The various steps of process 300 will now be discussed in turn.

Figure 2C:
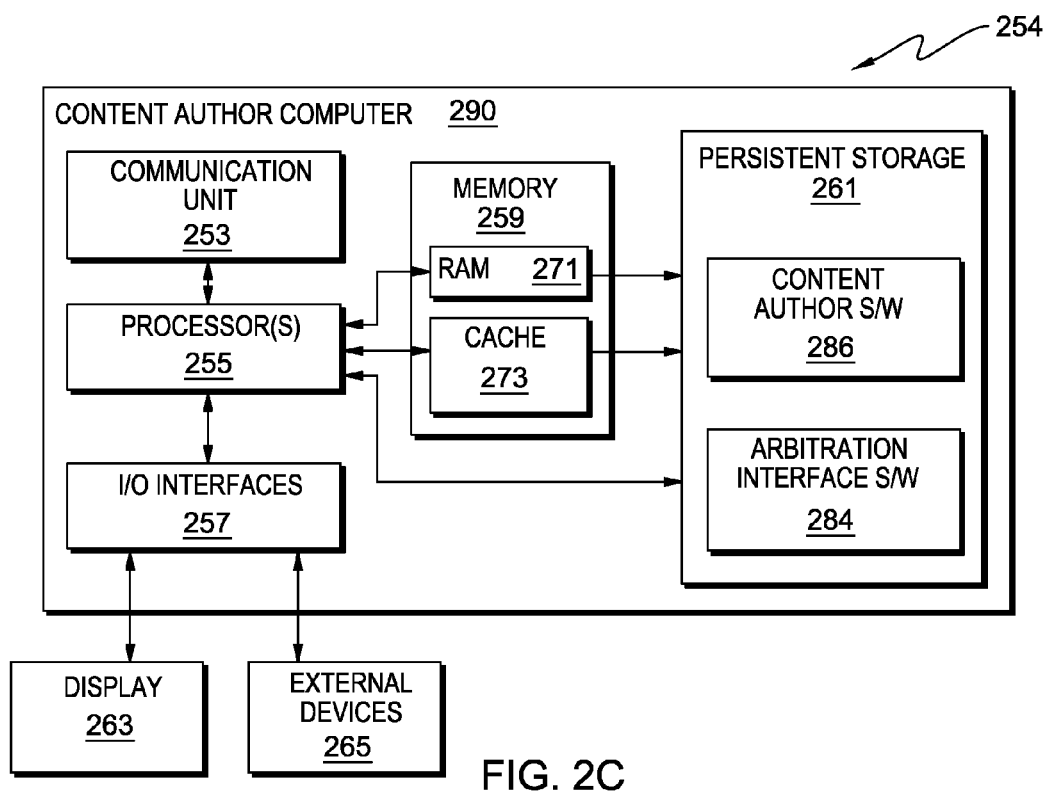
FIG. 2C is a schematic view of a portion of the distributed data processing system of FIG. 1.

The content creation step S301 identifies the creation of on-line content, such as for the Internet. The amount of content that is available on the Internet is voluminous. The content has all been created by entities, such as one or both of authors 108 and 110. A few examples of entities include, but are not limited to: (i) a person; (ii) a group of people; (iii) a computer algorithm(s); (iv) a legal entity, such as a corporation; or (v) a governmental unit. The authors 108 and 110 have a computer such as content author computer 290 of computer sub-system 254, as shown in FIG. 2c. Content author s/w (software) 286, which creates on-line content, includes, but is not limited to: (i) word processors; (ii) spreadsheet editors; (iii) browser page editors; (iv) video and still photo editors; and so on and so forth. After authors 108 and 110 create content, the content may be hosted on, for example, content hosting service 112.

Once content is hosted on content hosting service 112, the content may be available for aggregation. In most contexts, an aggregator, such as one or both of aggregators 104 and 106, refers to a website or computer software that aggregates a specific type of information from multiple online sources, such as content hosting service 112. Examples of aggregators 104 include: (i) data aggregator, an organization involved in assembling information from detailed databases on individuals and selling that information to others; (ii) news aggregator, a computer software or website that aggregates news from other news sources; (iii) poll aggregator, a website that aggregates polling data for upcoming elections; (iv) review aggregator, a website that aggregates reviews of movies or other products or services; (v) search aggregator, software that runs on a user's computer and fetches, filters, and organizes a specific search from various search engines; (vi) social network aggregation, the collection of content from multiple social network services; or (vii) a video aggregator, a website that collects and organizes online video sources. The two basic steps to assemble content, aggregator search S302 and aggregator assembles content S303, are accomplished via collection s/w 280 and aggregation s/w 282.

There are many aggregators that combine heterogeneous data in an attempt to form a complete story—such as CNN.com or CNBC.com (each of which can perform the functions of both aggregator 104 and content author 108). For instance, if a news aggregator wants to run a story about a United States political election, the news aggregator would assemble pertinent information in the United States and international mainstream media about election-related politics, political candidates, and current events, as well as, links to columnists concerning the subject. Some aggregators exclusively use computers to search and obtain their content, while others rely on personnel, and still others utilize a hybrid approach. Regardless of the aggregation subject matter or assembly method, there exists a content author and a content rights holder for the aggregated content. Generally, only the content owner has the ability to grant rights to the material. The rights might have been transferred, either manually or automatically, to another entity. To name one automatic assignment, many companies have agreements with employees such that any material created by them while in the employment of the company is the property of the company. Some companies extend this agreement to include a number of years after the employee-employer relationship has ended. In various embodiments the content author and the content rights holder may be, or may not be, the same entity; however, hereinafter for the purpose of discussion they are considered to be one in the same.

After the process of content assembly in aggregator search S302 and aggregator assembles content S303, the question arises as to whether the aggregator 104 has permission to use the content, as characterized by aggregator determines rights unknown S304. The permissions (the rights associated with the content) are varied and may be complex. A few examples of rights include, but are not limited to: (i) reuse-as-is; (ii) reuse-freely; (iii) reuse-with-permission; (iv) reuse-with-privacy; (v) reuse per-service; (vi) no-reuse; (vii) reuse-as-is-with-identification; (viii) reuse-with-modification-identification; and (ix) unknown.

Sophisticated aggregation software can present information in ways that were previously difficult, if not impossible. In order to accommodate new ways of presentation, rights need to be extendable as production software programs become even richer in displaying content formation and style. Rights may be agreed upon, ad hoc, between parties, as aggregator 104 develops novel and meaningful online presentations. For example, suppose the author 108, FIG. 1, is willing to allow reuse, as long as his website is linked to from the location where the reuse occurs, e.g., aggregator 104. In other words, the content can be reused as long as there is attribution to the author and the author's content is not modified (i.e. extract a summary out of an article and insert new hyperlinks inside the text). Consequently, an extended right from reuse-as-is would be reuse-as-is-with-attribution-link. This extended right can be negotiated between, for example, author 108 and arbitrator 102 to facilitate use of the content at aggregator 104.

The spectrum of content rights varies from reuse-freely to no-reuse. Although, the permissions within the scale of reuse-freely to no-reuse appear clear and definite, they can be ambiguous and questionable. For instance, reuse-with-privacy may signify: (i) the content can be reused as-long-as the author becomes anonymous; (ii) any identification of individuals referred within the content is expunged, as in blurring out faces; (iii) the information is only used within an organization; (iv) or any combination of the above. Another example of a right that is thought of as unequivocal, but is actually extendable, is when the right is no-reuse. For example, the owner 108 might consider allowing an aggregator 104 to use the content in a group with other similar content, thus, no-reuse, in this instance, should be replaced by an extended version that is adapted to new situations and that can be negotiated by arbitrator 102. On the other side of the spectrum, the right to reuse-freely may cause unanticipated issues with the author 108. For instance, an aggregator 104 may reveal the most common periods of activity for an author 108, which may cause problems with that author's employer or relatives. Many different kinds of information can be serendipitously revealed in an aggregation with reuse-freely rights. It is common for an aggregator 104 to summarize and represent content in diverse ways that were not originally envisioned by the content hosting services 112, and also differently than originally authorized by the authors 108 of the content. This ambiguity leads to hesitation and indecisiveness on the part of the aggregator 104 and deficient aggregation of content. Therefore, aggregators 104 need content that is clear of ambiguous rights. Nevertheless, relying on aggregators 104 to aggregate data in all of the possible interesting and relevant ways, and then determine permission, places a considerable burden on the development agility of such organizations, which in some cases may significantly delay or even prevent the creation of channels that would benefit the original authors 108 in ways they did not anticipate.

After determining that the rights for at least some of the content assembled in step aggregator assembles content S303 are unknown in step aggregator determines rights unknown S304, processing proceeds to step aggregator asks arbitrator S305, FIG. 3. This step involves the aggregator 104, FIG. 1, asking arbitrator 102 whether the assembled content is allowed to be used in a certain manner or usage. For instance, using a former example, an aggregator 104 may ask arbitrator 102 if it is permissible to reveal the most common periods of activity for an author 108. The arbitrator 102 would address the issue as to whether the usage of content that would reveal the most common periods of activity for an author 108 is allowable. This embodiment of the present invention provides a service that is focused on discovering if the rights associated with the content in question are determinate for a particular use of such content. In other words, aggregator 104 can request authorization to reuse content from other services and consult about the current authorization terms of content with the arbitrator 102. Further, aggregator 104 can ask arbitrator 102 about any kind of extended rights for assembled content.

The arbitration service s/w 240 contains the code for maintaining, storing, and accessing information in an information store, and the methods necessary to provide arbitrator 102. There is no need for all aggregators 104 to keep track of rights for today's large number of content hosting services 112 and content authors 108 and 110, because of the centralizing features of arbitrator 102 as discussed herein. The information store includes, but not limited to: (i) author's identification information, such as name, address, email, etc.; (ii) copies of content; (iii) rights associated with the content; (iv) extended rights, such as how original rights need to be modified; (v) date of entry; (vi) active flag, rather than replacing complete information records could be made inactive as newer records take precedence. The arbitration service s/w 240 may refer to an information store in the form of a: (i) database; (ii) flat file; (iii) or any structure that would facilitate access to the information. The information within the information store is obtainable through methods, whether custom or off-the-shelf, that facilitate access by authorized users. For example, such methods include, but are not limited to, a structured query language (SQL) interface.

As shown on FIG. 3, step aggregator asks arbitrator S305 is the first stage of determining whether the extended rights exist to use the plurality of content in the aggregation. In particular, aggregator 104 may communicate with arbitrator 102 via the arbitration interface s/w 284, which is the means to communicate among the computer sub-system 201, FIG. 2a, the computer sub-system 251, FIG. 2b, and the computer sub-system 254, FIG. 2c. The arbitration interface s/w 284 of the arbitrator 102 may vary considerably in its interface method among aggregators 104 and authors 108. The methods include, but are not limited to: (i) human interaction, such as a telephone conversion; (ii) interaction using a fax machine; (iii) communication over a network: such as emailing requests and responses, or off-the-shelf or custom-developed applications that allow data transferring; and (iv) using computer browsers for the inquiries and responses. For instance, using a browser an aggregator 104 can submit a freeform question along with contact information. If the arbitrator 102 includes a previous customer record for the aggregator 104, the aggregator 104 might simply supply a customer identification along with the freeform question. The freeform question may also include certain pre-determined checkboxes that would assist the arbitrator 102 in determining the exact rights required. The aggregator 104 can also supply any mock pages, or example pages from previous aggregations, that would facilitate the rights determination.

The aggregator 104 is not the only entity that utilizes the arbitrator 102. Authors 108 and 110, content hosting services 112, and even content consumers 113, may utilize the information store of arbitrator 102. For instance, author 110 might be curious as to how his content rights are listed with the arbitrator 102. In a similar inquiry, content consumers 113, whom might be considering becoming authors, could check with the arbitrator 102 on how similar content, that he is contemplating creating, is used in aggregations and its associated rights.

Step aggregator asks arbitrator S305 may occur in parallel with steps S304 and S303, or afterward. For example, in one embodiment aggregator 104 assembles content from content hosting services 112, while checking with arbitrator 102 whether the content is pre-authorized in terms of license by the owner for the intended use by aggregation service 104. The actual time period when the checking with the arbitrator 102 occurs may vary considerably among aggregators 104. The time period includes, but is not limited to: (i) simultaneously; (ii) near simultaneously; (iii) in an agreed upon time-of-day (perhaps at noon Eastern Standard Time); (iv) and once-a-day (perhaps a dump of all requests once a day).

After step aggregator asks arbitrator S305, processing proceeds on to step arbitrator finds rights S306. When content is not cleared for usage in the arbitrator 102, e.g., because arbitrator 102 does not include a record of any rights, or any extended rights, for the queried content, then the arbitrator 102 contacts the content hosting service 112 to check whether the license terms around the content allow for its usage in the intended manner (e.g. "can the content be used for statistic analysis in aggregate?" or "can the content be republished without modification and with attribution?"). During step arbitrator finds rights S306 arbitrator 102 can also attempt to negotiate new extended rights with content hosting service 112.

Proceeding to step arbitrator determines extended rights S307, FIG. 3. If the content hosting service 112 indicates to arbitrator 102 that the answer is contingent on author approval, the arbitrator 102 initiates contact with the author (e.g., author 108 or 110) to request approval for that intended usage, and to negotiate extended rights, at the same time informing the aggregator 104 that approval is pending. The outcomes to this inquiry include, but are not limited to: (i) the author 108 or 110 may grant the use based upon pre-existing rights; (ii) the author 108 or 110 may grant extended rights based upon an extension of previous rights (such as in the former example of reuse-as-is-with-attribution-link); (iii) the author 108 or 110 may deny the use of the content; and (iv) the author 108 or 110 does not respond. Notwithstanding the results of the inquiry, the arbitrator transmits the results, such as permitting the use of the plurality of content in the aggregation.

After step arbitrator determines extended rights S307, processing proceeds on to content is aggregated with appropriate rights S308. Based upon the response from the arbitrator 102 the aggregator 104 may include the content in an aggregation, or leave the content out of an aggregation. The aggregator 104 may eliminate the content from the aggregated content for each author 108 or 110 who has declined to grant the rights.

Now that the embodiment(s) of FIGS. 1 to 3 have been fully discussed, some additional discussion and/or embodiments of the present invention will be discussed in the following paragraphs.

Figure 4:
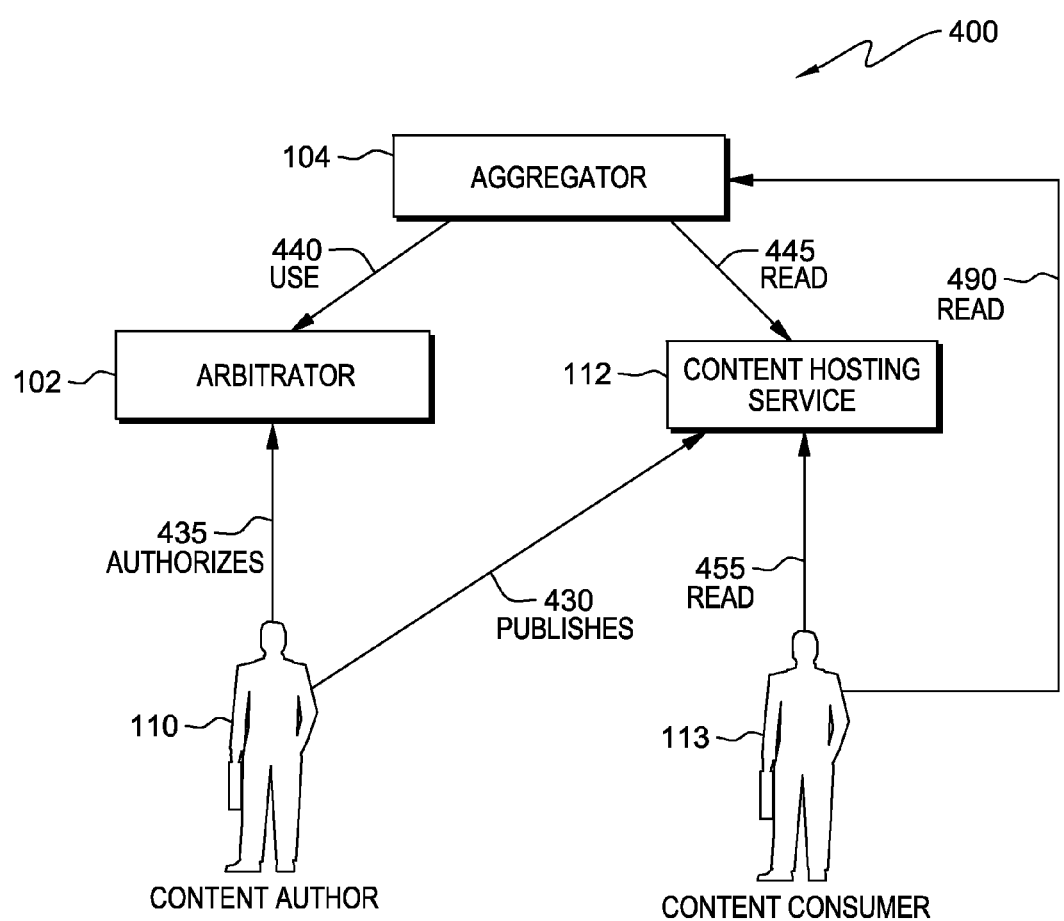
FIG. 4 is a schematic view of a distributed data processing system and transactions according to an embodiment of the present invention.

FIG. 4 will now be discussed in detail. As shown in FIG. 4, diagram 400, as another embodiment of the present invention, includes: author 110; arbitrator 102; aggregator 104; content hosting service 112; and content consumer 113. Diagram 400 depicts several transactions including: authorizes 435; use 440; read 445; read 490; read 455; and publishes 430.

Diagram 400 shows the interactions among the different entities. Content author 110 publishes 430 content to the content hosting service 112. Content consumer 113 reads 455 content from a content hosting service 112 and reads 490 from aggregator 104. Aggregator 104 also reads 445 from the content hosting service 112 in order to assemble content. Aggregator 104 asks the arbitrator 102 about the rights of the content the aggregator 104 wants to use via use 440. The arbitrator 102 asks the content author 110 about granting the use of the content via authorizes 435.

Rather than placing the burden on aggregators 104 the invention addresses the enablement of a syndication model that orchestrates the requirements from sources of content and content hosting services 112 in ways that allows authors 110 to retain control of their content without stifling the creation of new services. The arbitrator 102 is responsible for reaching out to the aggregator 104 and/or author 110 to explain how the data will be utilized and whether the aggregator 104 or author 110 approves of that usage.

The arbitrator 102 is responsible for hosting information on permissible usages of entries by a given author 110 and service. As examples, an aggregator 104 may consult the arbitrator 102 on whether the content of a content hosting service 112 can be reused in aggregate or whether an individual entry can be reused in a way that it can be traced to an author 108 or 110.

An aggregator 104 is a derivative service that exposes the data from a content hosting service 112 in different ways, enabling different visualizations or different operations against some representation of the original data.

A content hosting service 112 can be an online magazine or social bookmarking website providing a public data retrieval API (Application Programming Interface) of some sort, such as Atom or RSS (Really Simple Syndication).

An author 110 is a person who authors original content, such as tagging a bookmark in a social bookmarking tool, authoring a blog entry on a blog service, commenting to an article on an online magazine, etc. The author 110 explicitly authorizes the usage of his content through the lifecycle of the content. In some countries, the author 110 retains exclusive copyright-style rights over the content, in other cases content hosting services 112 may require that the user authorizes public availability of the work as a condition of publication.

A content consumer 113 is a person who reads, views, listens to, or otherwise experiences the content provided by either a content hosting service 112 or by an aggregator 104.

Figure 5:
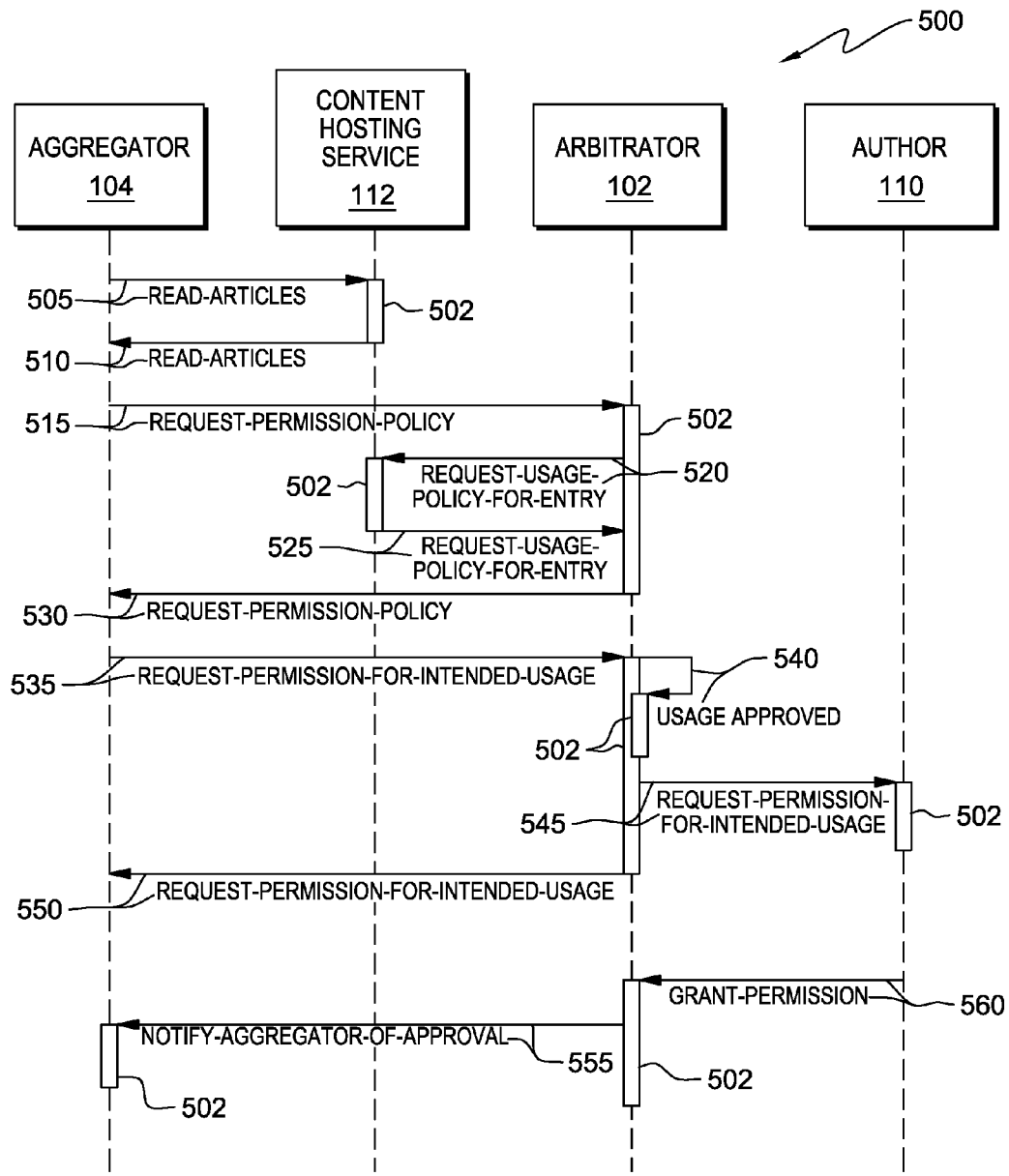
FIG. 5 is an event diagram depicting operation of the distributed data processing system according to an embodiment of the present invention.

FIG. 5 will now be discussed in detail. FIG. 5 is an event diagram depicting the order of interactions among the online participants. As shown in FIG. 5, diagram 500 includes: aggregator 104; content hosting service 112; arbitrator 102; author 110; multiple timing blocks 502; read-articles interface 505; read-articles interface 510; request-permission-policy interface 515; request-usage-policy-for-entry interface 520; request-user-policy-for-entry interface 525; request-permission-policy interface 530; request-permission-for-intended usage interface 535; usage approved 540; request-permission-for-intended usage interface 545; request-permission-for-intended usage interface 550; notify-aggregator-of-approval 555; and grant-permission interface 560. At request-permission-for-intended-usage interface 550, the response will indicate all approved usages and signal that a request for broader usage has been sent to the content author or content author could not be located. Further, after notify-aggregator-of-approval 555, the aggregation service is cleared to reuse the original content for the intended purpose.

The flowchart and block diagrams in the foregoing Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A computer system for providing rights management for electronic content in aggregation, the computer system comprising:

a non-transitory computer readable storage medium and program instructions stored on the non-transitory computer readable storage medium, the program instructions comprising:
   program instructions to receive, at an arbitrator computer, from an aggregator computer, communicating over an arbitration interface, a request for an intended use of a plurality of electronic content in an aggregation, wherein the plurality of electronic content is retrieved from multiple electronic sources using a public data retrieval Application Programming Interface (API), upon discovering rights associated with at least a portion of the electronic content are determinate for the intended use;
   program instructions to determine, by the arbitrator computer, whether the aggregator computer has permission for the intended use of the plurality of electronic content in the aggregation, wherein the permission for the intended use is based on a rule of the arbitrator computer stating whether a portion of information associated with an author is revealed, when the plurality of electronic content is aggregated;
   responsive to determining, by the arbitrator computer, that there is no rule of the arbitrator computer associated with the requested intended use of the plurality of electronic content in the aggregation, program instructions to contact, by the arbitrator computer, a content hosting service for the plurality of electronic content to determine, by the arbitrator computer, if the intended use or another intended use of the plurality of electronic content is permitted;
   responsive to determining, by the arbitrator computer, that the intended use of the plurality of electronic content is permitted contingent upon author approval, program instructions to contact, by the arbitrator computer, the author to obtain author approval; and
   program instructions to transmit, from the arbitration interface of the arbitrator computer, a reply to the arbitration interface of the aggregator computer, identifying a use of the plurality of electronic content that is permitted in the aggregation.

2. The computer system of claim 1, wherein the program instructions to determine, by the arbitrator computer, whether the aggregator computer has permission for the intended use of the plurality of electronic content in the aggregation further comprises:
   program instructions to determine, by the arbitrator computer, whether an information data store of the arbitrator computer contains additional rights for the intended use of the plurality of electronic content.

3. The computer system of claim 1, further comprising:
program instructions to negotiate, by the arbitrator computer, additional rights associated with the intended use of the plurality of electronic content, with the content hosting service or the author.

4. The computer system of claim 3, wherein:
the additional rights are based on a right previously granted by the author.

5. The computer system of claim 4, wherein the additional rights comprise: reuse-as-is, reuse-freely, reuse-with-permission, reuse-with-privacy, reuse per-service, no-reuse, reuse-as-is-with-identification, and reuse-with-modification-identification.

6. A rights management software, stored on a software storage device that stores data in a form more persistent than a signal in transit, the rights management software including program instructions comprising:
   program instructions to receive, at an arbitrator computer, from an aggregator computer, communicating over an arbitration interface, a request for an intended use of a plurality of electronic content in an aggregation, wherein the plurality of electronic content is retrieved from multiple electronic sources using a public data retrieval Application Programming Interface (API), upon discovering rights associated with at least a portion of the electronic content are determinate for the intended use;
   program instructions to determine, by the arbitrator computer, whether the aggregator computer has permission for the intended use of the plurality of electronic content in the aggregation, wherein the permission for the intended use is based on a rule of the arbitrator computer stating whether a portion of information associated with an author is revealed, when the plurality of electronic content is aggregated;
   responsive to determining, by the arbitrator computer, that there is no rule of the arbitrator computer associated with the requested intended use of the plurality of electronic content in the aggregation, program instructions to contact, by the arbitrator computer, a content hosting service for the plurality of electronic content to determine, by the arbitrator computer, if the intended use or another intended use of the plurality of electronic content is permitted;
   responsive to determining, by the arbitrator computer, that the intended use of the plurality of electronic content is permitted contingent upon author approval, program instructions to contact, by the arbitrator computer, the author to obtain author approval; and
   program instructions to transmit, from the arbitration interface of the arbitrator computer, a reply to the arbitration interface of the aggregator computer, identifying a use of the plurality of electronic content that is permitted in the aggregation.

7. The software of claim 6, wherein the program instructions to determine, by the arbitrator computer, whether the aggregator computer has permission for the intended use of the plurality of electronic content in the aggregation further comprises:
   program instructions to determine, by the arbitrator computer, whether an information data store of the arbitrator computer contains additional rights for the intended use of the plurality of electronic content.

8. The software of claim 6, further comprising:
program instructions to negotiate, by the arbitrator computer, additional rights associated with the intended use of the plurality of electronic content, with the content hosting service or the author.

9. The software of claim 8, wherein:
the additional rights are based on a right previously granted by the author.

10. The software of claim 9, wherein the additional rights comprise: reuse-as-is, reuse-freely, reuse-with-permission, reuse-with-privacy, reuse per-service, no-reuse, reuse-as-is-with-identification, and reuse-with-modification-identification.

11. The software of claim 6, further comprising:
program instructions to access, by one or more of: an aggregator computer, an author, a content hosting service, and a content consumer, rights for the intended use of the plurality of electronic content that are stored on an information store of the arbitrator computer.

* * * * *